(12) United States Patent
Govari et al.

(10) Patent No.: US 8,608,735 B2
(45) Date of Patent: Dec. 17, 2013

(54) CATHETER WITH ARCUATE END SECTION

(75) Inventors: Assaf Govari, Haifa (IL); Shahram Moaddeb, Irvine, CA (US); Michael Olen Zirkle, Yorba Linda, CA (US); Christopher Beeckler, Brea, CA (US); Philippa Hill, Pasadena, CA (US); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 806 days.

(21) Appl. No.: 12/649,417

(22) Filed: Dec. 30, 2009

(65) Prior Publication Data

US 2011/0160719 A1   Jun. 30, 2011

(51) Int. Cl.
*A61B 18/18* (2006.01)

(52) U.S. Cl.
USPC .................................. 606/41; 606/45; 606/42

(58) Field of Classification Search
USPC ....................................................... 606/32–45
See application file for complete search history.

(56) References Cited

U.S. PATENT DOCUMENTS

| | | |
|---|---|---|
| 3,971,364 A | 7/1976 | Fletcher et al. |
| 4,488,561 A | 12/1984 | Doring |
| 4,764,114 A | 8/1988 | Jeffcoat et al. |
| 4,856,993 A | 8/1989 | Maness et al. |
| 4,917,102 A | 4/1990 | Miller et al. |
| 4,917,104 A | 4/1990 | Rebell |
| 5,263,493 A | 11/1993 | Avitall |
| 5,368,564 A | 11/1994 | Savage |
| 5,391,199 A | 2/1995 | Ben Haim |
| 5,487,757 A | 1/1996 | Truckai et al. |
| 5,499,542 A | 3/1996 | Morlan |
| 5,558,091 A | 9/1996 | Acker et al. |
| 5,563,354 A | 10/1996 | Kropp |
| 5,643,197 A | 7/1997 | Brucker et al. |
| 5,662,124 A | 9/1997 | Wilk |
| 5,673,695 A | 10/1997 | McGee et al. |
| 5,680,860 A | 10/1997 | Imran |
| 5,685,878 A | 11/1997 | Falwell et al. |
| 5,730,127 A | 3/1998 | Avitall |
| 5,769,843 A | 6/1998 | Abela et al. |
| 5,820,591 A | 10/1998 | Thompson et al. |
| 5,826,576 A | 10/1998 | West |

(Continued)

FOREIGN PATENT DOCUMENTS

| | | | |
|---|---|---|---|
| DE | 19750441 A | 6/1999 | |
| EP | 856292 A | 8/1998 | |

(Continued)

OTHER PUBLICATIONS

Extended European Search Report dated Nov. 15, 2012 from related European Application No. 12185274.3.

(Continued)

*Primary Examiner* — Linda Dvorak
*Assistant Examiner* — Amanda Scott
(74) *Attorney, Agent, or Firm* — Louis J. Capezzuto

(57) ABSTRACT

A medical device includes an insertion shaft, having a longitudinal axis and having a distal end adapted for insertion into a body of a patient. A resilient end section is fixed to the distal end of the insertion shaft and is formed so as to define, when unconstrained, an arc oriented obliquely relative to the axis and having a center of curvature on the axis. One or more electrodes are disposed at respective locations along the end section.

21 Claims, 4 Drawing Sheets

(56) References Cited

U.S. PATENT DOCUMENTS

| | | |
|---|---|---|
| 5,836,894 A | 11/1998 | Sarvazyan |
| 5,860,920 A | 1/1999 | McGee et al. |
| 5,860,974 A | 1/1999 | Abele |
| 5,865,815 A | 2/1999 | Tihon |
| 5,871,523 A | 2/1999 | Fleischman et al. |
| 5,902,248 A | 5/1999 | Millar et al. |
| 5,916,147 A | 6/1999 | Boury |
| 5,938,694 A | 8/1999 | Jaraczewski et al. |
| 5,944,022 A | 8/1999 | Nardella et al. |
| 5,964,757 A | 10/1999 | Ponzi |
| 5,974,320 A | 10/1999 | Ward et al. |
| 5,983,126 A | 11/1999 | Wittkampf |
| 6,002,955 A | 12/1999 | Willems et al. |
| 6,048,329 A | 4/2000 | Thompson et al. |
| 6,063,022 A | 5/2000 | Ben Haim |
| 6,064,902 A | 5/2000 | Haissaguerre et al. |
| 6,123,699 A | 9/2000 | Webster, Jr. |
| 6,171,277 B1 | 1/2001 | Ponzi |
| 6,177,792 B1 | 1/2001 | Govari et al. |
| 6,183,463 B1 | 2/2001 | Webster, Jr. |
| 6,198,974 B1 | 3/2001 | Webster, Jr. |
| 6,201,387 B1 | 3/2001 | Govari |
| 6,203,493 B1 | 3/2001 | Ben Haim |
| 6,216,027 B1 | 4/2001 | Willis et al. |
| 6,226,542 B1 | 5/2001 | Reisfeld |
| 6,239,724 B1 | 5/2001 | Doron et al. |
| 6,241,724 B1 | 6/2001 | Fleischman et al. |
| 6,267,781 B1 | 7/2001 | Tu |
| 6,272,371 B1 | 8/2001 | Shlomo |
| 6,272,672 B1 | 8/2001 | Conway |
| 6,301,496 B1 | 10/2001 | Reisfeld |
| 6,332,089 B1 | 12/2001 | Acker et al. |
| 6,335,617 B1 | 1/2002 | Osadchy et al. |
| 6,371,955 B1 | 4/2002 | Fuimaono et al. |
| 6,436,059 B1 | 8/2002 | Zanelli |
| 6,456,864 B1 | 9/2002 | Swanson et al. |
| 6,468,260 B1 | 10/2002 | Bumbalough et al. |
| 6,484,118 B1 | 11/2002 | Govari |
| 6,500,167 B1 | 12/2002 | Webster, Jr. |
| 6,522,933 B2 | 2/2003 | Nguyen |
| 6,551,302 B1 | 4/2003 | Rosinko et al. |
| 6,574,492 B1 | 6/2003 | Ben Haim et al. |
| 6,584,856 B1 | 7/2003 | Biter et al. |
| 6,592,581 B2 | 7/2003 | Bowe |
| 6,602,242 B1 | 8/2003 | Fung et al. |
| 6,612,992 B1 | 9/2003 | Hossack et al. |
| 6,618,612 B1 | 9/2003 | Acker et al. |
| 6,669,692 B1 | 12/2003 | Nelson et al. |
| 6,690,963 B2 | 2/2004 | Ben Haim et al. |
| 6,695,808 B2 | 2/2004 | Tom |
| 6,711,429 B1 | 3/2004 | Gilboa et al. |
| 6,712,815 B2 | 3/2004 | Sampson et al. |
| 6,723,094 B1 | 4/2004 | Desinger |
| 6,727,371 B2 | 4/2004 | Muller et al. |
| 6,814,733 B2 | 11/2004 | Schwartz et al. |
| 6,835,173 B2 | 12/2004 | Couvillon, Jr. |
| 6,892,091 B1 | 5/2005 | Ben Haim et al. |
| 6,908,464 B2 | 6/2005 | Jenkins et al. |
| 6,911,019 B2 | 6/2005 | Mulier et al. |
| 6,915,149 B2 | 7/2005 | Ben Haim |
| 6,945,956 B2 | 9/2005 | Waldhauser et al. |
| 6,964,205 B2 | 11/2005 | Papakostas et al. |
| 6,973,339 B2 | 12/2005 | Govari |
| 6,997,924 B2 | 2/2006 | Schwartz et al. |
| 7,008,401 B2 | 3/2006 | Thompson et al. |
| 7,008,418 B2 | 3/2006 | Hall et al. |
| 7,077,823 B2 | 7/2006 | McDaniel |
| 7,156,816 B2 | 1/2007 | Schwartz et al. |
| 7,235,070 B2 | 6/2007 | Vanney |
| 7,285,119 B2 | 10/2007 | Stewart et al. |
| 7,306,593 B2 | 12/2007 | Keidar et al. |
| 7,311,704 B2 | 12/2007 | Paul et al. |
| 7,397,364 B2 | 7/2008 | Govari |
| 7,419,489 B2 | 9/2008 | Vanney et al. |
| 7,481,774 B2 | 1/2009 | Brockway et al. |
| 7,517,349 B2 | 4/2009 | Truckai et al. |
| 7,536,218 B2 | 5/2009 | Govari et al. |
| 7,604,605 B2 | 10/2009 | Zvuloni |
| 7,681,432 B2 | 3/2010 | Hay et al. |
| 7,686,767 B2 | 3/2010 | Maschke |
| 8,066,702 B2 | 11/2011 | Rittman et al. |
| 8,083,691 B2 | 12/2011 | Goldenberg et al. |
| 2001/0047129 A1 | 11/2001 | Hall et al. |
| 2001/0047133 A1 | 11/2001 | Gilboa et al. |
| 2002/0002329 A1 | 1/2002 | Avitall |
| 2002/0022839 A1* | 2/2002 | Stewart et al. ............... 606/41 |
| 2002/0065455 A1 | 5/2002 | Ben Haim et al. |
| 2002/0068866 A1 | 6/2002 | Zikorus et al. |
| 2002/0165461 A1 | 11/2002 | Hayzelden et al. |
| 2002/0193781 A1 | 12/2002 | Loeb |
| 2003/0105453 A1 | 6/2003 | Stewart et al. |
| 2003/0120195 A1 | 6/2003 | Milo et al. |
| 2003/0130615 A1 | 7/2003 | Tom |
| 2003/0158494 A1 | 8/2003 | Dahl et al. |
| 2003/0216722 A1 | 11/2003 | Swanson |
| 2004/0049255 A1 | 3/2004 | Jain et al. |
| 2004/0064024 A1 | 4/2004 | Sommer |
| 2004/0068178 A1 | 4/2004 | Govari |
| 2004/0082948 A1 | 4/2004 | Stewart et al. |
| 2004/0097806 A1 | 5/2004 | Hunter et al. |
| 2004/0102769 A1 | 5/2004 | Schwartz et al. |
| 2004/0143175 A1 | 7/2004 | Coleman et al. |
| 2004/0147920 A1 | 7/2004 | Keidar |
| 2004/0152974 A1 | 8/2004 | Solomon et al. |
| 2004/0244464 A1 | 12/2004 | Hajdukiewicz et al. |
| 2004/0254458 A1 | 12/2004 | Govari |
| 2005/0004565 A1 | 1/2005 | Vanney |
| 2005/0010095 A1 | 1/2005 | Stewart et al. |
| 2005/0033135 A1 | 2/2005 | Govari |
| 2005/0070894 A1 | 3/2005 | McClurken |
| 2005/0080429 A1 | 4/2005 | Freyman et al. |
| 2005/0187544 A1 | 8/2005 | Swanson et al. |
| 2005/0277875 A1 | 12/2005 | Selkee |
| 2006/0009690 A1 | 1/2006 | Fuimaono et al. |
| 2006/0009735 A1 | 1/2006 | Viswanathan et al. |
| 2006/0015096 A1 | 1/2006 | Hauck et al. |
| 2006/0020264 A1 | 1/2006 | Crowley et al. |
| 2006/0106295 A1 | 5/2006 | Jais et al. |
| 2006/0173480 A1 | 8/2006 | Zhang |
| 2006/0200049 A1 | 9/2006 | Leo et al. |
| 2006/0235381 A1 | 10/2006 | Whayne et al. |
| 2006/0247618 A1 | 11/2006 | Kaplan et al. |
| 2006/0253116 A1* | 11/2006 | Avitall et al. ............... 606/41 |
| 2007/0021742 A1 | 1/2007 | Viswanathan |
| 2007/0060832 A1 | 3/2007 | Levin |
| 2007/0060847 A1 | 3/2007 | Leo et al. |
| 2007/0100332 A1 | 5/2007 | Paul et al. |
| 2007/0106114 A1 | 5/2007 | Sugimoto et al. |
| 2007/0142749 A1 | 6/2007 | Khatib et al. |
| 2007/0151391 A1 | 7/2007 | Larkin et al. |
| 2007/0156114 A1 | 7/2007 | Worley et al. |
| 2007/0161882 A1 | 7/2007 | Pappone |
| 2007/0179492 A1 | 8/2007 | Pappone |
| 2007/0185397 A1 | 8/2007 | Govari et al. |
| 2007/0191829 A1 | 8/2007 | McGee et al. |
| 2007/0197939 A1 | 8/2007 | Wallace et al. |
| 2007/0282211 A1 | 12/2007 | Ofek et al. |
| 2008/0009750 A1 | 1/2008 | Aeby et al. |
| 2008/0015568 A1 | 1/2008 | Paul et al. |
| 2008/0051704 A1 | 2/2008 | Patel et al. |
| 2008/0065111 A1 | 3/2008 | Blumenkranz et al. |
| 2008/0071267 A1 | 3/2008 | Wang et al. |
| 2008/0077049 A1 | 3/2008 | Hirshman |
| 2008/0097394 A1 | 4/2008 | Lampropoulos et al. |
| 2008/0161774 A1 | 7/2008 | Hastings et al. |
| 2008/0161795 A1 | 7/2008 | Wang et al. |
| 2008/0183075 A1 | 7/2008 | Govari et al. |
| 2008/0249522 A1 | 10/2008 | Pappone et al. |
| 2008/0255540 A1 | 10/2008 | Selkee |
| 2008/0275428 A1 | 11/2008 | Tegg et al. |
| 2008/0275442 A1 | 11/2008 | Paul et al. |
| 2008/0275465 A1 | 11/2008 | Paul et al. |
| 2008/0281319 A1 | 11/2008 | Paul et al. |
| 2008/0287777 A1 | 11/2008 | Li et al. |

(56) References Cited

U.S. PATENT DOCUMENTS

| | | |
|---|---|---|
| 2008/0288038 A1 | 11/2008 | Paul et al. |
| 2008/0294144 A1 | 11/2008 | Leo et al. |
| 2008/0294158 A1 | 11/2008 | Pappone et al. |
| 2009/0010021 A1 | 1/2009 | Smith et al. |
| 2009/0093806 A1 | 4/2009 | Govari et al. |
| 2009/0138007 A1 | 5/2009 | Govari |
| 2009/0158511 A1 | 6/2009 | Maze et al. |
| 2009/0254083 A1 | 10/2009 | Wallace et al. |
| 2009/0287118 A1 | 11/2009 | Malek |
| 2009/0306650 A1 | 12/2009 | Govari et al. |
| 2010/0030209 A1 | 2/2010 | Govari et al. |
| 2010/0063478 A1 | 3/2010 | Selkee |
| 2010/0137845 A1 | 6/2010 | Ramstein et al. |
| 2010/0152574 A1 | 6/2010 | Erdman et al. |
| 2010/0168548 A1 | 7/2010 | Govari |
| 2010/0168620 A1 | 7/2010 | Klimovitch et al. |
| 2010/0168918 A1 | 7/2010 | Zhao et al. |
| 2010/0222859 A1 | 9/2010 | Govari |
| 2011/0054287 A1 | 3/2011 | Schultz |
| 2011/0054446 A1 | 3/2011 | Schultz |
| 2011/0130648 A1 | 6/2011 | Beeckler et al. |
| 2011/0144639 A1 | 6/2011 | Govari et al. |
| 2011/0184406 A1 | 7/2011 | Selkee |
| 2012/0053403 A1 | 3/2012 | Ducharme et al. |
| 2012/0143088 A1 | 6/2012 | Schultz |
| 2012/0172703 A1 | 7/2012 | Esguerra et al. |
| 2013/0006238 A1 | 1/2013 | Ditter et al. |

FOREIGN PATENT DOCUMENTS

| | | |
|---|---|---|
| EP | 928601 A | 7/1999 |
| EP | 1042990 A | 10/2000 |
| EP | 1181896 A | 2/2002 |
| EP | 1502555 A1 | 2/2005 |
| EP | 1586281 A | 10/2005 |
| EP | 1690564 A | 8/2006 |
| EP | 1743575 A | 1/2007 |
| EP | 1820464 A | 8/2007 |
| EP | 1897581 A | 3/2008 |
| EP | 2000789 A | 12/2008 |
| EP | 2047797 A | 4/2009 |
| EP | 2127604 A | 12/2009 |
| EP | 2130508 A | 12/2009 |
| EP | 2171240 A | 4/2010 |
| EP | 2 229 904 A1 | 9/2010 |
| EP | 2289403 A | 3/2011 |
| EP | 2289408 A | 3/2011 |
| EP | 2338411 A | 6/2011 |
| EP | 2338412 A | 6/2011 |
| JP | 2005345215 A | 12/2005 |
| JP | 2006064465 A | 3/2006 |
| WO | 95/10326 A | 4/1995 |
| WO | WO 96/05768 | 2/1996 |
| WO | 97/29678 A | 8/1997 |
| WO | 97/29709 A | 8/1997 |
| WO | 97/29710 A | 8/1997 |
| WO | 98/29032 A | 7/1998 |
| WO | 99/56812 A | 11/1999 |
| WO | 03/020139 A | 3/2003 |
| WO | 2006/003216 A | 1/2006 |
| WO | 2006/029563 A | 3/2006 |
| WO | 2006/086152 A | 8/2006 |
| WO | 2006/092563 A | 9/2006 |
| WO | 2007/025230 A | 3/2007 |
| WO | 2007/050960 A | 5/2007 |
| WO | 2007/067938 A | 6/2007 |
| WO | 2007/082216 A | 7/2007 |
| WO | 2007/098494 A | 8/2007 |
| WO | 2007/111182 A | 10/2007 |
| WO | 2009/078280 A | 6/2009 |
| WO | 2009/085470 A | 7/2009 |
| WO | 2009/147399 A | 12/2009 |
| WO | 2010/008975 A | 1/2010 |

OTHER PUBLICATIONS

Office Action dated Nov. 14, 2012 received from the European Patent Office from related European Application No. 10 252 246.3.

Biter, W.J. et al., "Magnetic Wire Strain Sensor," 33rd International Sample Technical Conference, Nov. 2001, vol. 33, pp. 12-23, Seattle, WA.

Biter, W.J. et al. "Magnetic Wire for Monitoring Strain in Composites," Sensors, Jun. 2001, www.sensormag.com, pp. 110-114.

Okumura, Y. et al. "A Systematic Analysis of in Vivo Contact Forces on Virtual Catheter Tip-Tissue Surface Contact During Cardiac Mapping and Intervention," J. of Cardiovasc Electrophysiol, vol. 19, pp. 632-640, Jun. 2008.

English abstract of DE 19750441 A, Jun. 10, 1999.

European Patent Convention Communication dated Aug. 29, 2013, from corresponding European Application No. 10 252 246.3.

European Patent Convention Communication dated Aug. 29, 2013, from corresponding European Application No. 12 185 274.3.

* cited by examiner

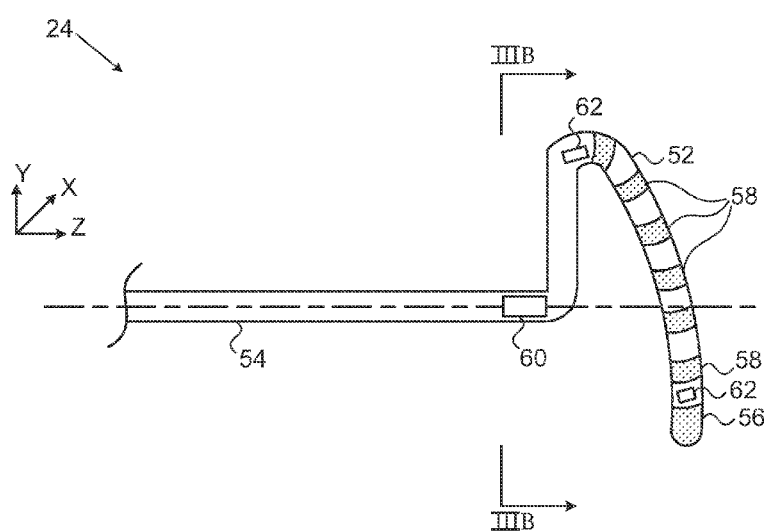 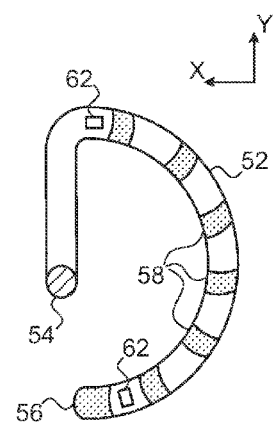
FIG. 3A
FIG. 3B

CATHETER WITH ARCUATE END SECTION

FIELD OF THE INVENTION

The present invention relates generally to methods and devices for invasive medical treatment, and specifically to catheters.

BACKGROUND OF THE INVENTION

Ablation of myocardial tissue is well known as a treatment for cardiac arrhythmias. In radio-frequency (RF) ablation, for example, a catheter is inserted into the heart and brought into contact with tissue at a target location. RF energy is then applied through an electrode on the catheter in order to create a lesion for the purpose of breaking arrhythmogenic current paths in the tissue.

Recently, circumferential ablation of the ostia of the pulmonary veins has gained acceptance as a treatment for atrial arrhythmias, and particularly for atrial fibrillation. For example, U.S. Pat. No. 6,064,902, whose disclosure is incorporated herein by reference, describes a catheter for ablating tissue on the inner wall of a blood vessel, such as a pulmonary vein. The tip portion of the catheter is deflectable from a first, generally straight, configuration, in which the proximal and distal sections are substantially co-linear, to a second, J-shaped, configuration in which the proximal and distal sections are generally parallel with a separation therebetween substantially corresponding to the inside diameter of the blood vessel. The distal end portion of the catheter is rotated about the longitudinal axis of the catheter to cause a circumferential displacement of proximal and distal ablation electrodes on the catheter along the inner wall of the pulmonary vein. In this way, the electrode catheter may be used to ablate a number of circumferentially-spaced sites on the inner wall of the pulmonary vein by ablating one or two sites at each circumferential position.

U.S. Patent Application Publication 2005/0033135, whose disclosure is incorporated herein by reference, describes a lasso for pulmonary vein mapping and ablation. A catheter for circumferentially mapping a pulmonary vein (PV) includes a curved section shaped to generally conform to the shape of the interior surface of the PV. The curved section comprises one or more sensing electrodes, and its proximal end is joined at a fixed or generally known angle to a base section of the catheter. Position sensors are fixed to the curved section of the catheter and to the distal end of the base section. The catheter is inserted into the heart, and the curved section is positioned in contact with the wall of the PV, while the base section remains within the left atrium, typically positioned such that the joint with the curved section is at the ostium of the vein. The information generated by the three position sensors is used to calculate the locations and orientations of the sensing electrodes, which enables mapping of the surface of the PV. The sensing electrodes may additionally perform ablation of selected sites, or the catheter may further comprise ablation elements.

U.S. Pat. No. 7,008,401, whose disclosure is incorporated herein by reference, describes compound steering assemblies, usable in both diagnostic and therapeutic applications, for steering the distal section of a catheter in multiple planes or complex curves. These assemblies are said to enable a physician to swiftly and accurately position and maintain ablation and/or mapping electrodes in intimate contact with an interior body surface. U.S. Pat. No. 5,820,591, whose disclosure is incorporated herein by reference, similarly describes compound steering assemblies of this sort.

SUMMARY OF THE INVENTION

Embodiments of the present invention that are described hereinbelow provide invasive devices and methods for contacting tissue within the body with enhanced ease and reliability.

There is therefore provided, in accordance with an embodiment of the present invention, a medical device, including an insertion shaft, having a longitudinal axis and having a distal end adapted for insertion into a body of a patient. A resilient end section is fixed to the distal end of the insertion shaft and is formed so as to define, when unconstrained, an arc oriented obliquely relative to the axis and having a center of curvature on the axis. One or more electrodes are disposed at respective locations along the end section.

In one embodiment, the arc subtends more than 300°. In other embodiments, the arc subtends less than 270°, and possibly 180°. Typically, the end section includes a base, which is connected to the distal end of the insertion shaft, and a tip, and has a helical form such that the tip protrudes axially in a distal direction relative to the base.

In some embodiments, the one or more electrodes include a tip electrode extending over the tip and a plurality of proximal electrodes distributed along the end section. The end section is configured so that when the unconstrained end section is advanced axially against a tissue surface in the body, the end section engages the tissue surface along the arc so that the tip electrode and at least some of the proximal electrodes contact the tissue surface simultaneously. Optionally, the end section includes one or more joints, which can be straightened and steered so as to bring the tip electrode alone into contact with the tissue surface.

In a disclosed embodiment, the device includes at least one position transducer, and possibly a plurality of position transducers distributed within the end section.

There is also provided, in accordance with an embodiment of the present invention, a medical device, including an insertion shaft, having a longitudinal axis and having a distal end adapted for insertion through a body passage into a cavity within a body of a patient. A resilient end section includes a base, which is connected to the distal end of the insertion shaft, and a tip, and is formed so as to define, when unconstrained, an arc that is oriented obliquely relative to the axis and has a helical form such that the tip protrudes axially in a distal direction relative to the base. One or more electrodes are disposed at respective locations along the end section.

There is additionally provided, in accordance with an embodiment of the present invention, medical apparatus, including a probe for insertion into a body of a patient. The probe includes an insertion shaft, having a longitudinal axis and having a distal end adapted for insertion into the body. A resilient end section is fixed to the distal end of the insertion shaft and is formed so as to define, when unconstrained, an arc oriented obliquely relative to the axis and having a center of curvature on the axis. One or more electrodes are disposed at respective locations along the end section and configured to contact tissue in the body. A radio frequency (RF) generator is coupled to supply RF energy through the probe to at least one of the electrodes so as to ablate the tissue.

In a disclosed embodiment, the probe includes a position transducer in the end section, and the apparatus includes a position sensing system, which is configured to communicate with the position transducer so as to determine a position of the end section within the body.

In some embodiments, the apparatus includes a sheath, which is configured to be inserted through a body passage into a cavity within the body, and the probe is configured to be inserted through the sheath into the cavity. In one embodiment, the sheath is configured to be inserted through a blood vessel into a chamber of a heart, and wherein the end section is configured to engage, along the arc, a tissue in the chamber. Typically, the insertion shaft is configured to be rotated about the axis within the sheath, so as to cause the arc to describe an annular path on the tissue.

There is further provided, in accordance with an embodiment of the present invention, a method for medical treatment, including inserting into a body of a patient a probe including an insertion shaft, having a longitudinal axis and a distal end, and a resilient end section, which is fixed to the distal end of the insertion shaft and is formed so as to define, when unconstrained, an arc oriented obliquely relative to the axis and having a center of curvature on the axis, with electrodes disposed at respective locations along the end section. The probe is advanced axially so that the end section engages a tissue in the body along the arc, causing at least some of the electrodes to contact the tissue simultaneously. The insertion shaft is rotated about the axis, so as to cause the arc to describe an annular path on the tissue while the at least some of the electrodes contact the tissue.

In disclosed embodiments, the method includes applying energy through the electrodes so as to ablate the tissue along the annular path. In one embodiment, inserting the probe includes passing the probe through a blood vessel into a chamber of a heart and tracing the annular path around an ostium of a pulmonary vein in a left atrium of the heart.

The present invention will be more fully understood from the following detailed description of the embodiments thereof, taken together with the drawings in which:

BRIEF DESCRIPTION OF THE DRAWINGS

FIGS. 3A and 3B are schematic side and sectional views, respectively, of a catheter, in accordance with an embodiment of the present invention.

DETAILED DESCRIPTION OF EMBODIMENTS

Overview

Figure 1:
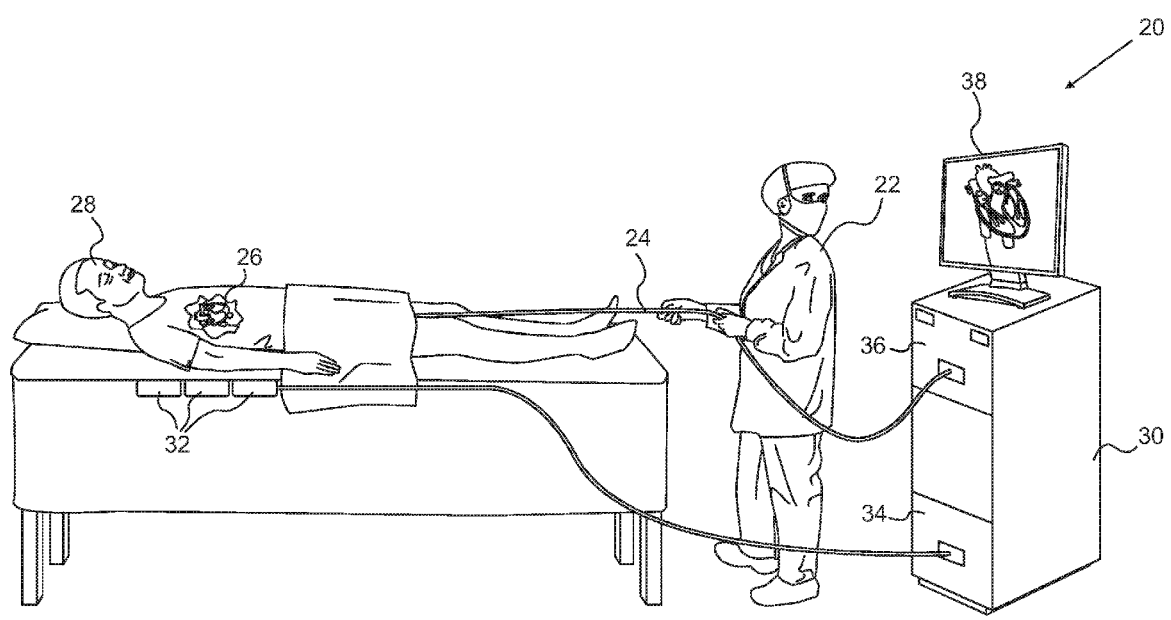
FIG. 1 is a schematic pictorial illustration of a system for ablation of tissue in the heart, in accordance with an embodiment of the present invention.

Lasso catheters, as described above, may be used for ablating tissue along an arc surrounding an anatomical structure, such as the ostium of a pulmonary vein. The lasso is generally made thin and flexible, for purposes of maneuverability, with large ring electrodes to minimize electrical resistance. U.S. patent application Ser. No. 12/345,720, filed Dec. 30, 2008, which is assigned to the assignee of the present patent application and whose disclosure is incorporated herein by reference, describes an alternative design in which the lasso is thicker and stiffer. Even so, operators often find lasso catheters to be difficult to maneuver within the heart, and particularly difficult to position in such a way that the entire circumference of the lasso is in contact with the tissue, as is desirable for effective pulmonary vein isolation, for example.

Embodiments of the present invention that are described hereinbelow provide probes, such as catheters, with improved lasso-type structures to facilitate maneuvering and positioning of the structure in the heart. Such catheters can be used to produce curved ablation paths, as well as sensing electrical activity at points along a curve.

In the disclosed embodiments, a catheter comprises an insertion shaft having a longitudinal axis. A resilient end section, with electrodes disposed along its length, is fixed to the distal end of the insertion shaft. This end section is formed so as to define, when unconstrained, an arc oriented obliquely relative to the longitudinal axis of the insertion shaft and having a center of curvature on the axis. The term "oblique," in the context of the present patent application and in the claims, means that the plane in space that best fits the arc is angled relative to the shaft axis. The angle between the plane and the axis is typically at least 45°, and in the embodiments shown below is approximately 90°.

An operator inserts the catheter into a body cavity, such as a heart chamber, and advances the distal end of the catheter axially toward a tissue in the body, such as the inner heart wall. (The term "axial" refers to the direction parallel to the longitudinal axis of the insertion shaft.) As a result, the end section of the catheter will engage the tissue surface frontally along the arc, and some or all of the electrodes on the end section will thus contact the tissue surface simultaneously.

For improved contact, the arc may have a helical form, whereby the distal tip of the end section protrudes axially in the distal direction relative to the base of the end section, which connects to the insertion shaft (i.e., when the end section is unconstrained, the tip is slightly ahead of the base). The helical form is compressed axially and thus flattened as the end section is advanced against the tissue, so that there is positive pressure between each of the electrodes and the tissue.

After bringing the end section into engagement with the tissue at the target location, the operator rotates the insertion shaft about its axis, thus causing the arc to describe an annular path on the tissue while the electrodes contact the tissue. Because the arc is centered on the axis, simple rotation of the shaft is sufficient to engender this annular motion, typically without the need for additional manipulation or steering of the catheter. In this manner, for example, the operator can cause the end section to trace an annular path around an anatomical feature, such as the ostium of a pulmonary vein in the left atrium. The operator may apply energy, such as radio frequency (RF) electrical current, through the electrodes so as to ablate the tissue along this annular path. This arrangement provides an easy and reliable way to create annular lesions in the tissue, as well as sensing signals along annular paths.

System Description

FIG. 1 is a schematic pictorial illustration of a system 20 for ablation of tissue in a heart 26 of a patient 28, in accordance with an embodiment of the present invention. An operator 22, such as a cardiologist, inserts a catheter 24 through the vascular system of patient 28 so that the distal end of the catheter enters a chamber of the patient's heart. Operator 22 advances the catheter so that the end section of the catheter engages endocardial tissue at a desired location or locations, as shown in the figures that follow. Catheter 24 is connected by a suitable connector at its proximal end to a console 30. The console comprises a RF generator 36 for applying RF energy through electrodes on the end section of the catheter in order to ablate the tissue contacted by the distal section. Alternatively or additionally, catheter 24 may be used for other diagnostic and/or therapeutic functions, such as intracardiac electrical mapping or other types of ablation therapy.

In the pictured embodiment, system 20 uses magnetic position sensing to determine position coordinates of the end section of the catheter inside heart 26. To determine the position coordinates, a driver circuit 34 in console 30 drives field generators 32 to generate magnetic fields within the body of patient 28. Typically, field generators 32 comprise coils, which are placed below the patient's torso at known positions external to the body. These coils generate magnetic fields in a predefined working volume that contains heart 26. One or more magnetic field sensors within the end section of catheter 24 (as shown in FIG. 3) generate electrical signals in response to these magnetic fields. The console processes these signals in order to determine the position (location and/or orientation) coordinates of the end section of catheter 24, and possibly also the deformation of the end section, as explained below. Console 30 may use the coordinates in driving a display 38 to show the location and status of the catheter. This method of position sensing and processing is described in detail, for example, in PCT International Publication WO 96/05768, whose disclosure is incorporated herein by reference, and is implemented in the CARTO™ system produced by Biosense Webster Inc. (Diamond Bar, Calif.).

Alternatively or additionally, system 20 may comprise an automated mechanism (not shown) for maneuvering and operating catheter 24 within the body of patient 28. Such mechanisms are typically capable of controlling both the longitudinal motion (advance/retract) and the rotation of catheter 24. In such embodiments, console 30 generates a control input for controlling the motion of the catheter based on the signals provided by the position sensing system.

Although FIG. 1 shows a particular system configuration, other system configurations may be used in alternative embodiments of the present invention. For example, the methods described hereinbelow may be applied using position transducers of other types, such as impedance-based or ultrasonic position sensors. The term "position transducer" as used herein refers to an element mounted on or in catheter 24 that causes console 30 to receive signals indicative of the coordinates of the element. The position transducer may thus comprise a receiver in the catheter, which generates a position signal to the control unit based on energy received by the transducer; or it may comprise a transmitter, emitting energy that is sensed by a receiver external to the probe. Furthermore, the methods described hereinbelow may similarly be applied in mapping and measurement applications using not only catheters, but also probes of other types, both in the heart and in other body organs and regions.

Figure 2:
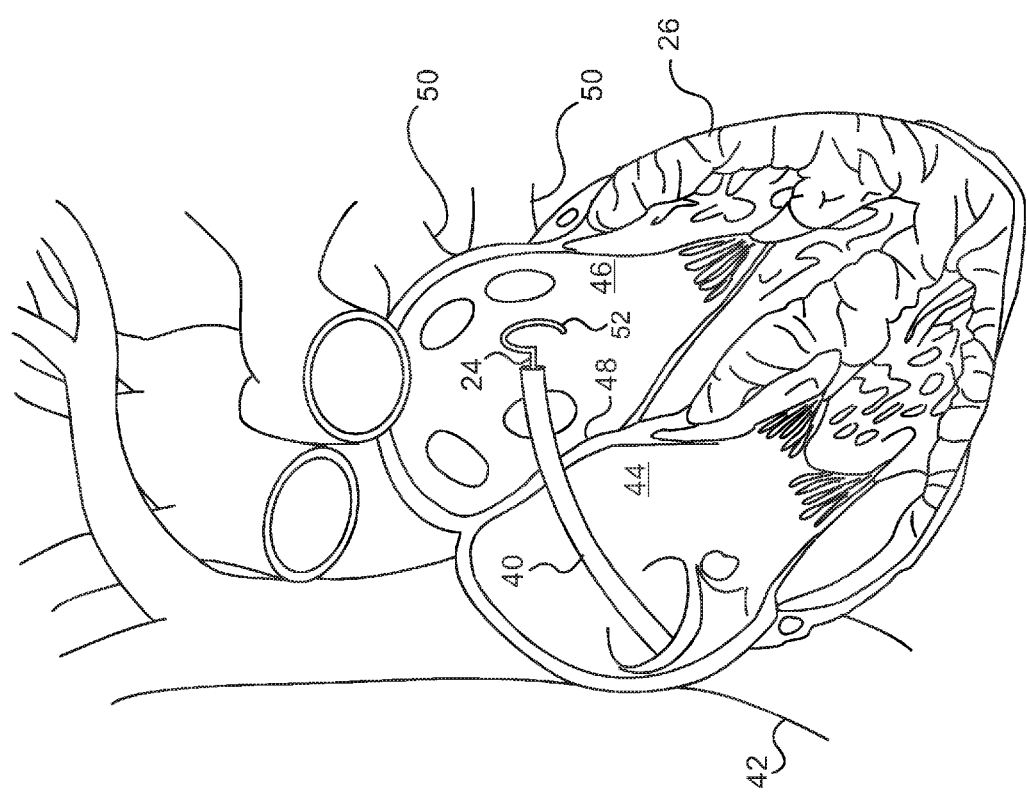
FIG. 2 is a schematic sectional view of a heart showing insertion of a catheter into the left atrium, in accordance with an embodiment of the present invention.

FIG. 2 is a schematic sectional view of heart 26, showing insertion of catheter 24 into the heart, in accordance with an embodiment of the present invention. To insert the catheter in the pictured embodiment, the operator first passes a sheath 40 percutaneously through the vascular system and into right atrium 44 of the heart through ascending vena cava 42. The sheath penetrates through interatrial septum 48, typically via the fossa ovalis, into left atrium 46. Alternatively, other approach paths may be used. Catheter 24 is then inserted through the sheath until an end section 52 of the catheter passes out of the distal opening at the end of the sheath into the left atrium, as shown in the figure. The end section is formed so as to define an arc when unconstrained, as is shown and described in greater detail hereinbelow.

Operator 22 aligns the longitudinal axis of sheath 40 (and of catheter 24) inside left atrium 46 with the axis of one of pulmonary veins 50. The operator may carry out this alignment using the position sensing methods described above, along with a pre-acquired map or image of heart 26. Alternatively or additionally, the alignment may be performed under fluoroscopic or other means of visualization. The operator advances end section 52 of the catheter toward the target pulmonary vein so that the arc contacts the ostium, so that the end section either partly or fully surrounds the vein (depending on the angle subtended by the arc). The operator then rotates the catheter about its axis within the sheath so that the end section traces an annular path around the circumference of the vein. Meanwhile, the operator actuates RF generator 36 to ablate the tissue along the path. After completing this procedure around one pulmonary vein, the operator may shift the sheath and catheter and repeat the procedure around one or more of the other pulmonary veins.

The above procedures may be carried out without the use of any steering mechanism in catheter 24: Due to the curved shape of the catheter, only advancement/retraction and rotation of the catheter are required. The absence of an internal steering mechanism reduces the size and cost of the catheter relative to devices that are known in the art. As noted earlier, the above procedures may be carried out by an automated mechanism, rather than manually by the operator as illustrated in FIG. 1.

Optionally, catheter 24 may contain a steering mechanism (not shown), which enables operator 22 to straighten the joints of end section 52. In this configuration, the operator may manipulate catheter 24 in order to trace (and possibly ablate) other sorts of paths or to sense or ablate tissue at specific, discrete points in the heart wall, either in left atrium 46 or elsewhere.

Catheter Structures

Reference is now made to FIGS. 3A and 3B, which schematically show details of the distal portion of catheter 24, in accordance with an embodiment of the present invention. FIG. 3A is a side view, while FIG. 3B is a cross-sectional view taken along a line IIIB-IIIB in FIG. 3A. The catheter comprises an insertion shaft 54, which connects at its distal end to the base of end section 52. The Z-axis in these figures is taken to be the longitudinal axis of the insertion shaft, as illustrated by a dashed line in FIG. 3A. End section 52 is oriented roughly in the X-Y plane but has a helical form so that the distal tip of section 52 protrudes axially (along the Z-axis) in the distal direction (to the right in FIG. 3A).

Shaft 54 and end section 52 typically comprise an outer shell made from a suitable flexible biocompatible material, such as polyurethane, having a diameter around 2-3 mm, with internal wires and tubing as required. In one embodiment, in which the catheter is designed for therapeutic ablation, the size of the shaft is 7 Fr (about 2.3 mm diameter), while the end section is of the same or slightly larger size (such as 7.5 Fr). In other embodiments, for diagnostic measurements, the shaft is 7 Fr, while the end section has a diameter between 1 and 2.5 mm.

End section 52 is formed as a partial lasso, i.e., as a preformed arcuate structure, which is centered on the axis of shaft 54 and loops through considerably less than 360°, and typically less than 270°. In the pictured embodiment, for example, the catheter ends in a "half-lasso" arc of about 180°. This sort of shape makes the end section easier to maneuver and position accurately. The radius of curvature of end section 52, when unconstrained, is typically between 7.5 mm and 15 mm. Because the arc structure is resilient and, possibly, slightly helical, when end section 52 is positioned in the heart (half surrounding the ostium of a pulmonary vein, for example), and insertion shaft 54 is advanced distally, the end section will press against the heart tissue over the entire length of the arc, thus facilitating good tissue contact.

The arcuate, helical shape of end section 52 may be maintained, for example, by incorporating a thin strut made from a shape memory material, such as Nitinol, in the desired shape (not shown in the figures) within the end section. The strut is typically made sufficiently flexible to permit the end section to straighten during insertion through sheath 40, and then to resume its arcuate form when it is unconstrained inside the heart chamber. Typically, the strut is designed so that an axial force of 5 grams or greater is required to flatten the helical shape so that the entire length of the arcuate end section presses against the tissue.

End section 52 comprises an array of electrodes along its length, including, in this example, a tip electrode 56 extending over the distal tip of the end section and proximal electrodes 58 distributed along the end section. Typically, the electrodes have a width between 1 mm and 4 mm, and are spaced between 1 mm and 10 mm apart. The electrodes are connected to the connector at the proximal end of catheter 24 by wires (not shown) running through the catheter. Alternatively, other electrode configurations may be used. For example, the end section may include only ring electrodes, without a tip electrode. As another example, the end section may include smaller "bump" electrodes, as described in the above-mentioned U.S. patent application Ser. No. 12/345,720. In any of these configurations, the electrodes may be used for sensing and/or ablation. In order to ablate an entire annulus around a pulmonary vein, for example, catheter 24 may be rotated ("clocked") about its axis, as noted above.

To provide local cooling and prevent adhesion during ablation, electrodes 56 and 58 may have perforations for irrigation. (Perforations of this type are described and shown in U.S. patent application Ser. No. 12/345,720.) The perforations are coupled to a lumen (not shown) in end section 52, which carries irrigation fluid from shaft 54 to the electrodes and to the tissue surrounding them. The pressure of irrigation fluid tends to be lower at the distal end of the end section than at the proximal. To counteract this pressure difference, the irrigation holes in the distal electrodes may be relatively larger and/or more numerous than in the proximal electrodes.

Optionally, end section 52 comprises an internal steering mechanism (not shown), which can be operated to straighten the joints of the end section and to bring tip electrode 56 alone into contact with the tissue surface. For example, the steering mechanism may comprise one or more pull-wires, which run through a lumen in the catheter, as is known in the art. (The catheter may contain multiple lumens, for pull-wires and the strut mentioned above, for irrigation fluid, and for electrical wires connected to the electrodes and position transducers.) When ablation or sensing at a single point is required, the tip electrode can be brought into contact with the point and actuated by itself. On the other hand, when the half-lasso configuration of FIGS. 3A and 3B is used, the tip electrode can be actuated along with the ring electrodes along the length of the end section. Thus, catheter 24 can be used for both individual points and for curved ablation and/or sensing paths, providing enhanced utility and versatility in carrying out different sorts of procedures.

Catheter 24 may also include one of more position transducers, such as positions sensors 60 and 62 shown in FIGS. 3A and 3B. In this embodiment, sensors 60 and 62 comprise coils, which output position signals in response to the magnetic fields of field generators 32 (FIG. 1). For example, sensor 60 may comprise three coils, which give full location and orientation information with regard to the base of end section 52, while sensors 62 comprise each comprise a single coil, giving location and partial orientation information. This sort of arrangement is described further in the above-mentioned U.S. Patent Application Publication 2005/0033135. It enables console 30 to track both the base location and the deformation of the end section, so that the operator can verify that the end section is properly located and in good contact with the tissue. Alternatively, other types of position transducers and sensing configurations may be used in catheter 24 and system 20.

Figure 4A:
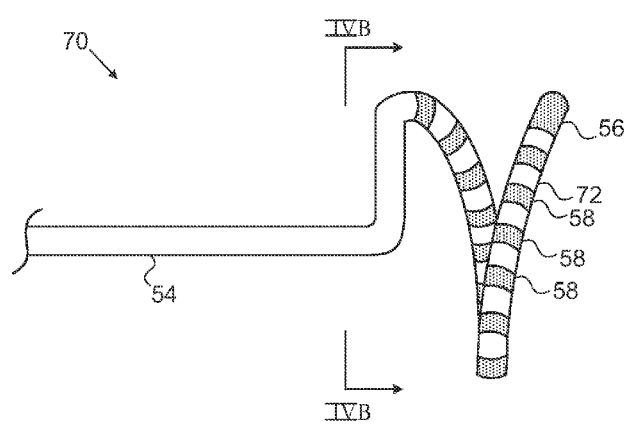
FIGS. 4A and 4B are schematic side and sectional views, respectively, of a catheter, in accordance with another embodiment of the present invention.
Figure 4B:
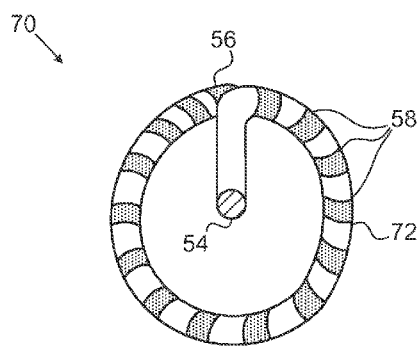

FIGS. 4A and 4B schematically illustrate the distal portion of a catheter 70, in accordance with another embodiment of the present invention. FIG. 4A is a side view, while FIG. 4B is a cross-sectional view taken along a line IVB-IVB in FIG. 4A. Certain elements of catheter 70, such as insertion shaft 54 and electrodes 56 and 58, are similar to the corresponding elements of catheter 24, as described above, and are therefore marked with the same numbers. Catheter 70 may have other features similar to those of catheter 24, such as internal struts, steering elements, position transducers, and various electrode types and irrigation, but these features have been omitted from the figures and from the present description for the sake of simplicity and brevity.

Catheter 70 differs from catheter 24 in that an arcuate end section 72 of catheter 70 is formed as a full (or nearly full) loop, subtending more than 300°, and possibly the full 360°. Therefore, end section 72 is capable of covering an entire annular ablation or sensing path with little or no rotation of shaft 54. End section 72, like end section 52 of catheter 24, is centered on the axis of shaft 54 and helical in shape. These features make the end section easier to position in the desired anatomical location and facilitate good contact between electrodes 58 and the target tissue over the entire length of the end section.

Although the embodiments described above relate specifically to catheters for use in certain intracardiac procedures, probes made in accordance with the principles set forth in this patent application may similarly be used in diagnostic and therapeutic procedures of other types, both in the heart and in other body organs. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A medical device, comprising:
   an insertion shaft, having a longitudinal axis and having a distal end adapted for insertion into a body of a patient;
   a resilient end section, which is fixed to the distal end of the insertion shaft and is formed so as to define, when unconstrained, an arc oriented obliquely relative to the axis and having a center of curvature on the axis, the arc having a radius of curvature, when unconstrained, between 7.5 mm and 15 mm; and
   one or more electrodes disposed at respective locations along the end section.

2. The device according to claim 1, wherein the arc subtends more than 300°.

3. The device according to claim 1, wherein the arc subtends less than 270°.

4. The device according to claim 3, wherein the arc subtends 180°.

5. The device according to claim 1, wherein the end section comprises a base, which is connected to the distal end of the insertion shaft, and a tip, and has a helical form such that the tip protrudes axially in a distal direction relative to the base.

6. The device according to claim 1, wherein the end section comprises a base, which is connected to the distal end of the insertion shaft, and a tip, and wherein the one or more electrodes comprise a tip electrode extending over the tip and a plurality of proximal electrodes distributed along the end section.

7. The device according to claim 6, wherein the end section is configured so that when the unconstrained end section is advanced axially against a tissue surface in the body, the end section engages the tissue surface along the arc so that the tip electrode and at least some of the proximal electrodes contact the tissue surface simultaneously.

8. The device according to claim 7, wherein the end section comprises one or more joints, which can be straightened and steered so as to bring the tip electrode alone into contact with the tissue surface.

9. The device according to claim 1, and comprising at least one position transducer.

10. The device according to claim 9, wherein the at least one position transducer comprises a plurality of position transducers distributed within the end section.

11. A medical device, comprising:
an insertion shaft, having a longitudinal axis and having a distal end adapted for insertion through a body passage into a cavity within a body of a patient;
a resilient end section, which comprises a base, which is connected to the distal end of the insertion shaft, and a tip, and which is formed so as to define, when unconstrained, an arc that is oriented obliquely relative to the axis and has a helical form such that the tip protrudes axially in a distal direction relative to the base; and
one or more electrodes disposed at respective locations along the end section, the one or more electrodes comprising a tip electrode extending over the tip and a plurality of proximal electrodes distributed along the end section,
wherein the end section is configured so that when the unconstrained end section is advanced axially against a tissue surface in the body, the end section engages the tissue surface along the arc so that the tip electrode and at least some of the proximal electrodes contact the tissue surface simultaneously,
wherein the insertion shaft is configured to be rotated about the axis, so as to cause the arc to describe an annular path on the tissue.

12. Medical apparatus, comprising:
a probe for insertion into a body of a patient, the probe comprising:
an insertion shaft, having a longitudinal axis and having a distal end adapted for insertion into the body;
a resilient end section, which is fixed to the distal end of the insertion shaft and is formed so as to define, when unconstrained, an arc oriented obliquely relative to the axis, subtending 180° and having a center of curvature on the axis; and
one or more electrodes disposed at respective locations along the end section and configured to contact tissue in the body; and
a radio frequency (RF) generator, which is coupled to supply RF energy through the probe to at least one of the electrodes so as to ablate the tissue.

13. The apparatus according to claim 12, wherein the probe comprises a position transducer in the end section, and wherein the apparatus comprises a position sensing system, which is configured to communicate with the position transducer so as to determine a position of the end section within the body.

14. The apparatus according to claim 12, and comprising a sheath, which is configured to be inserted through a body passage into a cavity within the body, and wherein the probe is configured to be inserted through the sheath into the cavity.

15. The apparatus according to claim 14, wherein the sheath is configured to be inserted through a blood vessel into a chamber of a heart, and wherein the end section is configured to engage, along the arc, a tissue in the chamber.

16. The apparatus according to claim 15, wherein the insertion shaft is configured to be rotated about the axis within the sheath, so as to cause the arc to describe an annular path on the tissue.

17. The apparatus according to claim 12, wherein the end section comprises a base, which is connected to the distal end of the insertion shaft, and a tip, and has a helical form such that the tip protrudes axially in a distal direction relative to the base.

18. A method for medical treatment, comprising: inserting into a body of a patient a probe comprising an insertion shaft, having a longitudinal axis and a distal end, and a resilient end section, which is fixed to the distal end of the insertion shaft and is formed so as to define, when unconstrained, an arc oriented obliquely relative to the axis and having a center of curvature on the axis, with electrodes disposed at respective locations along the end section; advancing the probe axially so that the end section engages a tissue in the body along the arc, causing at least some of the electrodes to contact the tissue simultaneously; and rotating the insertion shaft about the axis, so as to cause the arc to describe an annular path on the tissue while the at least some of the electrodes contact the tissue.

19. The method according to claim 18, and comprising applying energy through the electrodes so as to ablate the tissue along the annular path.

20. The method according to claim 18, wherein inserting the probe comprises passing the probe through a blood vessel into a chamber of a heart.

21. The method according to claim 20, wherein rotating the insertion shaft comprises tracing the annular path around an ostium of a pulmonary vein in a left atrium of the heart.

* * * * *